United States Patent
Xie et al.

(10) Patent No.: US 11,219,652 B2
(45) Date of Patent: Jan. 11, 2022

(54) METHOD FOR EXTRACTING HERBAL MEDICINE

(71) Applicants: Xiaolin Xie, Xi'an (CN); Dezhu Zhang, Xi'an (CN); Jianguo Meng, Xi'an (CN); Yu Wang, Xi'an (CN); Xuhua Zhou, Xi'an (CN); Zhong Meng, Xi'an (CN); Nan Hui, Xi'an (CN); Juan Li, Xi'an (CN)

(72) Inventors: Xiaolin Xie, Xi'an (CN); Dezhu Zhang, Xi'an (CN); Jianguo Meng, Xi'an (CN); Yu Wang, Xi'an (CN); Xuhua Zhou, Xi'an (CN); Zhong Meng, Xi'an (CN); Nan Hui, Xi'an (CN); Juan Li, Xi'an (CN)

(73) Assignee: SHAANXI PANLONG PHARMACEUTICAL GROUP LIMITED BY SHARE LTD., Xi'an (CN)

( * ) Notice: Subject to any disclaimer, the term of this patent is extended or adjusted under 35 U.S.C. 154(b) by 13 days.

(21) Appl. No.: 16/993,599

(22) Filed: Aug. 14, 2020

(65) Prior Publication Data

US 2020/0376056 A1 Dec. 3, 2020

Related U.S. Application Data

(62) Division of application No. 16/448,510, filed on Jun. 21, 2019, now Pat. No. 10,772,921.

(30) Foreign Application Priority Data

May 28, 2019 (CN) .......................... 201910453364.8

(51) Int. Cl.
*A61K 36/16* (2006.01)
*B01D 11/02* (2006.01)
(Continued)

(52) U.S. Cl.
CPC ............ *A61K 36/16* (2013.01); *B01D 11/028* (2013.01); *B01D 11/0288* (2013.01);
(Continued)

(58) Field of Classification Search
CPC .............. A61K 36/16; A61K 2236/333; A61K 2236/51; A61K 36/258; A61K 36/484; A61K 36/537; A61K 2236/331; A61K 36/899; A61K 36/51; A61K 36/2236; A61K 2236/30; A61K 2236/39; A61K 2236/50; A61K 2236/53; A61K 2236/55; B01D 11/028; B01D 11/0288; B01D 21/262; B01D 9/0054; B01D 9/0027; B01D 9/0059; B01D 11/0257; B01D 11/0292;
(Continued)

(56) References Cited

U.S. PATENT DOCUMENTS 2,505,139 A * 4/1950 Pascal .................... C11B 1/102
422/281
2,616,908 A * 11/1952 Colbeth ................... C11B 1/10
554/11
(Continued)

*Primary Examiner* — Joseph W Drodge

(57) ABSTRACT

A method for extracting herbal medicine includes: step one, spray extraction; step two, pressure filtration and concentration; step three, spray and countercurrent precipitation; and step four, concentrating reduced pressure and drying.

3 Claims, 2 Drawing Sheets

(51) Int. Cl.
  *B01D 37/00* (2006.01)
  *B01D 21/26* (2006.01)
(52) U.S. Cl.
  CPC .......... *B01D 21/262* (2013.01); *B01D 37/00* (2013.01); *A61K 2236/333* (2013.01); *A61K 2236/51* (2013.01)
(58) Field of Classification Search
  CPC .... B01D 21/2461; B01D 36/00; B01D 11/02; B01D 11/0215; B01D 11/0261; B01D 11/0269; B01D 11/0284; B01D 21/01; B01D 21/08; B01D 21/24; B01D 12/245; B01D 21/2488; B01D 21/26; B01D 21/28; B01D 33/01; B01D 33/015; B01D 33/04; B01D 33/80; B01D 36/02; B01D 36/04; B01D 36/045; B01D 37/00; B01D 2011/002; C11B 1/10; C11B 1/102; C11B 1/108; C11B 3/006; C11B 3/008
  See application file for complete search history.

(56) References Cited

U.S. PATENT DOCUMENTS

| | | | | |
|---|---|---|---|---|
| 3,394,647 | A * | 7/1968 | Reiter | C12C 7/165 99/278 |
| 3,436,319 | A * | 4/1969 | Von Horst | C12C 3/12 203/89 |
| 3,877,634 | A * | 4/1975 | Rohde | B04B 5/0421 494/1 |
| 5,773,075 | A * | 6/1998 | Todd | A23L 27/11 426/425 |
| 9,005,678 | B1 * | 4/2015 | Cao | A61K 36/54 424/725 |
| 10,512,856 | B1 * | 12/2019 | Jackson | C07D 311/80 |
| 10,772,921 | B1 * | 9/2020 | Liang | A61K 36/484 |
| 10,967,030 | B2 * | 4/2021 | Zhang | A61K 36/489 |
| 2003/0054070 | A1 * | 3/2003 | Bridges | A23L 33/155 426/73 |
| 2003/0185811 | A1 * | 10/2003 | Teasdale | A61K 36/06 424/93.45 |
| 2004/0175439 | A1 * | 9/2004 | Cyr | A61K 36/185 424/725 |
| 2005/0233011 | A1 * | 10/2005 | Beavers | A61K 36/29 424/725 |
| 2010/0317518 | A1 * | 12/2010 | Stevens | A01N 25/28 504/117 |
| 2012/0251470 | A1 * | 10/2012 | Kim | A61K 8/9794 424/62 |
| 2012/0285900 | A1 * | 11/2012 | Domanico | B01D 33/00 210/781 |
| 2012/0329138 | A1 * | 12/2012 | Van Kaathoven | C11B 1/00 435/252.5 |
| 2013/0079531 | A1 * | 3/2013 | Barringer | A61K 36/54 424/725 |
| 2016/0250564 | A1 * | 9/2016 | Thomas | B01D 1/14 554/8 |
| 2018/0071353 | A1 * | 3/2018 | Li | C07C 15/52 |
| 2018/0343812 | A1 * | 12/2018 | Leo | A01G 22/00 |
| 2019/0048101 | A1 * | 2/2019 | Nocera, Jr | B01D 15/26 |
| 2019/0167731 | A1 * | 6/2019 | Liu | A61K 36/65 |
| 2020/0080777 | A1 * | 3/2020 | McNeil | B01D 11/0296 |
| 2020/0085904 | A1 * | 3/2020 | Subramoni | A61K 36/9066 |
| 2020/0206652 | A1 * | 7/2020 | Corey | B01D 11/0219 |
| 2020/0282329 | A1 * | 9/2020 | Jiao | B01D 11/0288 |

* cited by examiner

METHOD FOR EXTRACTING HERBAL MEDICINE

The present invention is a Divisional Application of U.S. Ser. No. 16/448,510, filed on Jun. 21, 2019, which claims priority to Chinese Application No.: 201910453364.8, filed on May 28, 2019, which is incorporated by reference for all purposes as if fully set forth herein.

FIELD OF THE INVENTION

The present invention relates to a method for extracting herbal medicine.

BACKGROUND OF THE INVENTION

Solvent extraction method is a commonly used method to extract the active ingredients of traditional Chinese herbal medicine. Based on whether heating is applied, the extract method is divided into two types: cold extraction method and hot extraction method. The cold extraction method further includes impregnation method and percolation method, and is suitable for the extraction of the active ingredients that are unstable to heat. The cold extraction takes a long time and uses a large amount of solvent, and the extraction efficiency is low. The hot extraction method further includes boiling method, reflux method, and continuous extraction method, suitable for the extraction of heat-stable active ingredients. The reflux method is an important hot extraction method, but it takes a long time, and the active ingredients that are unstable to heat are easily decomposed and destroyed during the extraction. Fresh solvent is required for each batch. It is not suitable for continuous production. New extraction methods, such as supercritical fluid extraction, ultrasonic extraction and microwave-assisted extraction, have emerged, but these new extraction methods require expensive equipment and large investment and are not suitable for large scale production.

Common methods for separation and purification of active ingredients of traditional Chinese herbal medicine include extraction, precipitation, salting out, dialysis, crystallization, fractionation, etc. In recent years, new methods, such as supercritical fluid extraction, membrane separation, ultrafine pulverization technology, flocculation separation technology, semi-bionic extraction, ultrasonic extraction, cyclone extraction, pressurized counter-current extraction, enzymatic extract, macroporous resin adsorption, ultrafiltration, molecular distillation, have been used to separate and purify the active ingredients. Based on the nature of the active ingredients to be purified and the production need, one or two purification methods may be combined. For example, in a precipitation method, a reagent is added to an herbal medicine extract solution to produce a precipitate to either obtain an active ingredient or remove impurities. Water extracting and alcohol precipitation method or alcohol extraction and water precipitation method is often used to purify the active ingredients. After a reagent is added to the herbal medicine extract solution, the mixture was centrifuged and filtered. The extraction device and container are then cleaned for the next batch. The extraction operation is not continuous, and the active ingredient extract yield is low. There is a need for a continuous high efficiency herbal medicine extract method.

SUMMARY OF THE INVENTION

In one embodiment, the present invention provides a device for high pressure spray and counter-current precipitation extraction of herbal medicine. The device includes: an agitation tank (1); a first plunger pump (2); an extraction tank (3); a filter press (4); an extraction storage tank (5); an extracting solvent tank (6); a second plunger pump (7); a first centrifugal pump (8); a second centrifugal pump (9); a vacuum concentration tank (10); a third plunger pump (11); a tube centrifuge (12); a resting tank (17); a precipitation solvent storage tank (18); a four plunger pump (19); and an extraction waste discharge device. A bottom outlet of the agitation tank (1) is connected to a top inlet of the extraction tank (3) via the first plunger pump (2); an outlet of the extracting solvent tank (6) is connected to a lower solvent inlet of the extraction tank (3) via the second plunger pump (7); a bottom outlet of the extraction tank (3) is connected to an inlet of the filter press (4); an outlet of the filter press (4) is connected to an inlet of the extraction storage tank (5); an outlet of the extraction storage tank (5) is connected to an inlet of the vacuum concentration tank (10) via the first centrifugal pump (8); a solvent outlet of the vacuum concentration tank (10) is connected to an inlet of the extracting solvent tank (6) via the second centrifugal pump (9); an outlet of the vacuum concentration tank (10) is connected to a top inlet of the tube centrifuge (12) via the third plunger pump (11); a bottom inlet of the tube centrifuge (12) is connected to an outlet of the precipitation solvent storage tank (18) via the fourth plunger pump (19); an overflow outlet (20) of the tube centrifuge (12) is connected to an inlet of the resting tank (17); the extraction waste discharge device includes a spiral scraper (14), a differential (16), an inner tube (21), and an extraction waste discharge outlet (15); and a rotating tube (13) of the tube centrifuge (12) is connected to the differential (16), and the differential (16) is connected to the spiral scraper (14) via a shaft.

In another embodiment, the rotating tube (13) has a truncated cone shape and a half cone angle of 10 to 12°.

In another embodiment, the overflow outlet (20) has a diameter of 60 to 100 mm and has a center line that is perpendicular to a rotary axis of the rotating tube (13).

In another embodiment, the inner tube (21) has a double truncated cone shape, a bottom half cone angle that is the same as the half cone angle of the rotating tube (13), a top half cone angle of 60-65°, and a length that is one third of the length of the rotating tube (13).

In another embodiment, the spiral scraper (14) is a single-headed spiral made of a wear-resistant steel and has a blade thickness of 6-8 mm and a blade height of 30-35 mm, and a distance between the spiral scraper (14) and the rotating tune (13) is 1.5 mm to 2 mm.

In one embodiment, the present invention provides a method for extracting herbal medicine. The method includes step one, spray extraction; step two, pressure filtration and concentration; step three, spray and countercurrent precipitation; and step four, concentrating reduced pressure and drying.

Step one includes: pulverizing herbs to 100 to 120 mesh fine powder, adding the fine powder and an extracting solvent, in a ratio of 6-7 L extracting solvent/1 kg fine powder, to an agitation tank (1), stirring the mixture of the fine powder and extracting solvent at 80-100 r/min for 1-1.5 hours, spraying the mixture to an extraction tank (3) at a spraying speed of 400 to 600 L/h, two-thirds to three-fourths of the extraction tank (3) being filled with extraction solvent and the mixture being sprayed 2-3 cm below the surface of extracting solvent, spraying countercurrently the extracting solvent from the bottom of the extraction tank (3) at a speed of 1000-1600 L/h to form an extraction solution, the extracting solvent being pumped from an extracting solvent tank (6) at a pump pressure of 3.0-5.0 MPa, the extraction being conducted at room temperature.

Step two includes: discharging the extraction solution from step one to a filter press (4) to remove insoluble waste at a speed of 400-600 L/h and a pressure of 0.4-0.7 MPa to store at an extraction storage tank (5), pumping the extraction solution from the extraction storage tank (5) to a vacuum concentration tank (10), concentrating the extraction solution in the vacuum concentration tank (10) under −0.08 MPa--0.1 MPa and at 60-80° C. to form a concentrated extraction solution with a solution density of 1.0-1.3, the extracting solvent being recycled to the extracting solvent tank (6);

Step three includes: spraying the concentrated extraction solution to a tube centrifuge (12) at a speed of 200-400 L/h, two-thirds to three-fourths of the tube centrifuge (12) being filled with a precipitation solvent and the concentrated extraction solution being sprayed 2-3 cm below the surface of the precipitation solvent, spraying countercurrently the precipitation solvent from the bottom of the tube centrifuge (12) at a speed of 1000-1400 L/h and a pressure of 2.0-4.0 MPa to form a precipitation solution, centrifuging the precipitation solution and discharging a supernatant an overflow outlet (20) to a resting tank (17) at a speed of 600-900 L/h, the supernatant being stored in the resting tank (17) for 24 hours.

Step four includes: concentrating the supernatant from the resting tank (17) under reduced pressure, drying by vacuum spray and freeze-dry to obtain the herb medicine.

In another embodiment, the extracting solvent is water or 10% ethanol aqueous solution containing 0.5% ammonia.

In another embodiment, the precipitation solvent is 60% ethanol aqueous solution, 85% ethanol aqueous solution, anhydrous ethanol, or 98% sulfuric acid.

Compared with the prior art, the invention has the following advantages:

1. The extraction of the active ingredients of the herbal medicine by high pressure spray and counter-current precipitation extraction greatly increases the contact area between the extracting solvent and the herbs, increases the dissolution of the active ingredients of the herbal medicine, improves the extraction efficiency, and reduces the extraction time and the solvent usage. At the same time, spraying the solvent countercurrently achieves good stirring effect, which solves the disadvantages that pulverized herbs are prone to precipitate in the traditional extraction process.

2. The extraction solution is further purified by spraying precipitation solvent countercurrently and centrifugation in a tube centrifuge. The precipitation solvent is continuously flowed in a countercurrent flow to make the extraction solution and the precipitation solvent fully and effectively contact. The impurities are fully precipitated, and the product recovery rate is high and the quality is uniform.

3. Spray and countercurrent precipitation and centrifugation are conducted simultaneously in a tube centrifuge. Precipitation and centrifugal separation are conducted continuously. Production efficiency is greatly improved.

4. A spiral scraper is installed under the tube centrifuge. It solves the problem that extraction waste accumulates inside the tube centrifuge. Continuous production is achieved, and equipment utilization is improved.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

Figure 1:
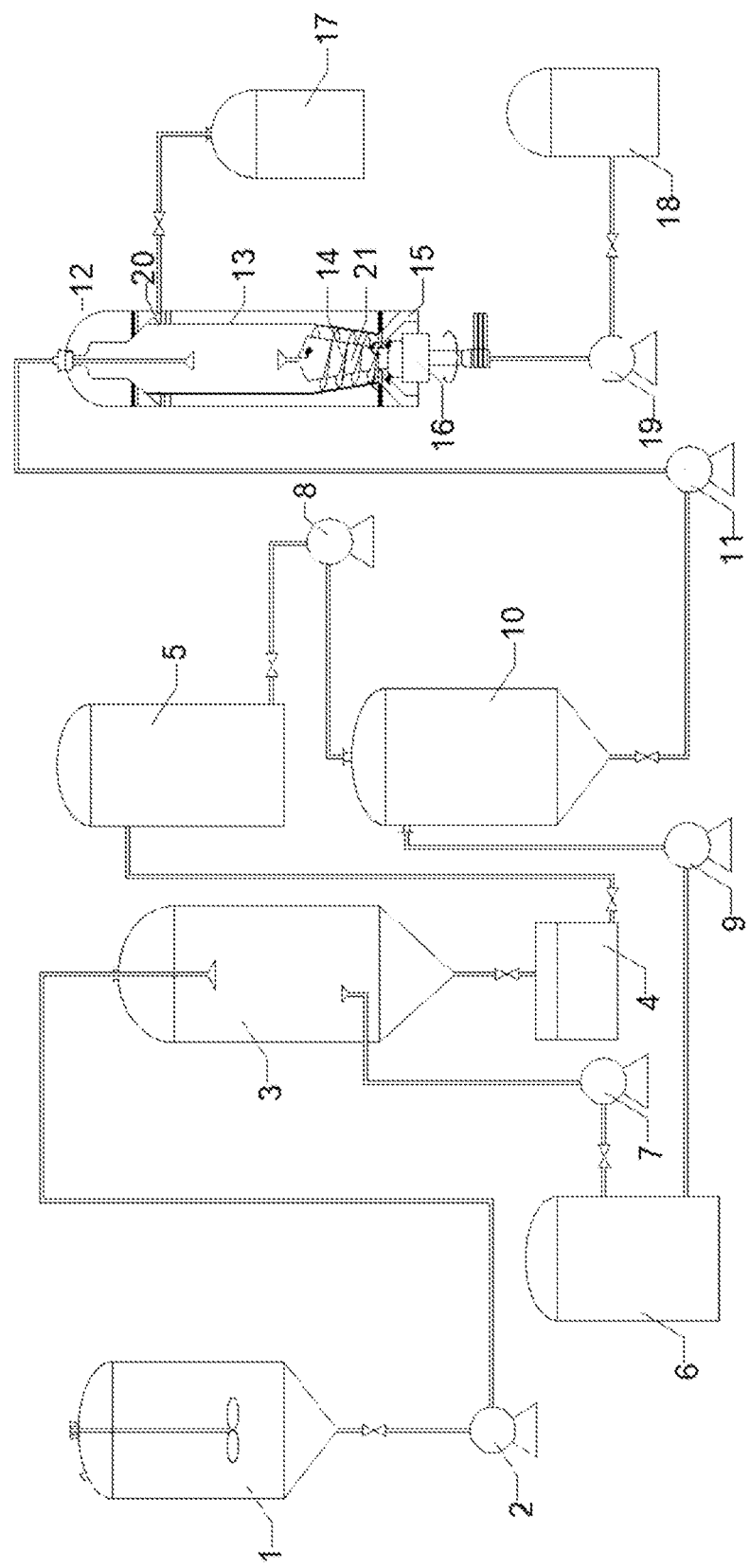
FIG. 1 shows a device for high pressure spray and counter-current precipitation extraction of herbal medicine.

REFERENCE NUMERALS (1) agitation tank; (2) plunger pump; (3) extraction tank; (4) filter press; (5) extraction storage tank; (6) extracting solvent tank; (7) plunger pump; (8) centrifugal pump; (9) centrifugal pump; (10) vacuum concentration tank; (11) plunger pump; (12) tube centrifuge; (13) rotating tube; (14) spiral scraper; (15) extraction waste discharge outlet; (16) differential; (17) resting tank; (18) precipitation solvent storage tank; (19) plunger pump; (20) overflow outlet; and (21) inner tube.

DETAILED DESCRIPTION OF THE ILLUSTRATED EMBODIMENTS

Reference will now be made in detail to embodiments of the present invention, example of which is illustrated in the accompanying drawings.

Referring to FIG. 1, a device for high pressure spray and counter-current precipitation extraction of herbal medicine includes an agitation tank (1); a first plunger pump (2); an extraction tank (3); a filter press (4); an extraction storage tank (5); an extracting solvent tank (6); a second plunger pump (7); a first centrifugal pump (8); a second centrifugal pump (9); a vacuum concentration tank (10); a third plunger pump (11); a tube centrifuge (12); a resting tank (17); a precipitation solvent storage tank (18); a fourth plunger pump (19); and an extraction waste discharge device. A bottom outlet of the agitation tank (1) is connected to a top inlet of the extraction tank (3) via the first plunger pump (2); an outlet of the extracting solvent tank (6) is connected to a lower solvent inlet of the extraction tank (3) via the second plunger pump (7); a bottom outlet of the extraction tank (3) is connected to an inlet of the filter press (4); an outlet of the filter press (4) is connected to an inlet of the extraction storage tank (5); an outlet of the extraction storage tank (5) is connected to an inlet of the vacuum concentration tank (10) via the first centrifugal pump (8); a solvent outlet of the vacuum concentration tank (10) is connected to an inlet of the extracting solvent tank (6) via the second centrifugal pump (9); an outlet of the vacuum concentration tank (10) is connected to a top inlet of the tube centrifuge (12) via the third plunger pump (11); a bottom inlet of the tube centrifuge (12) is connected to an outlet of the precipitation solvent storage tank (18) via the fourth plunger pump (19); an overflow outlet (20) of the tube centrifuge (12) is connected to an inlet of the resting tank (17); the extraction waste discharge device includes a spiral scraper (14), a differential (16), an inner tube (21), and an extraction waste discharge outlet (15); and a rotating tube (13) of the tube centrifuge (12) is connected to the differential (16), and the differential (16) is connected to the spiral scraper (14) via a shaft.

Figure 2:
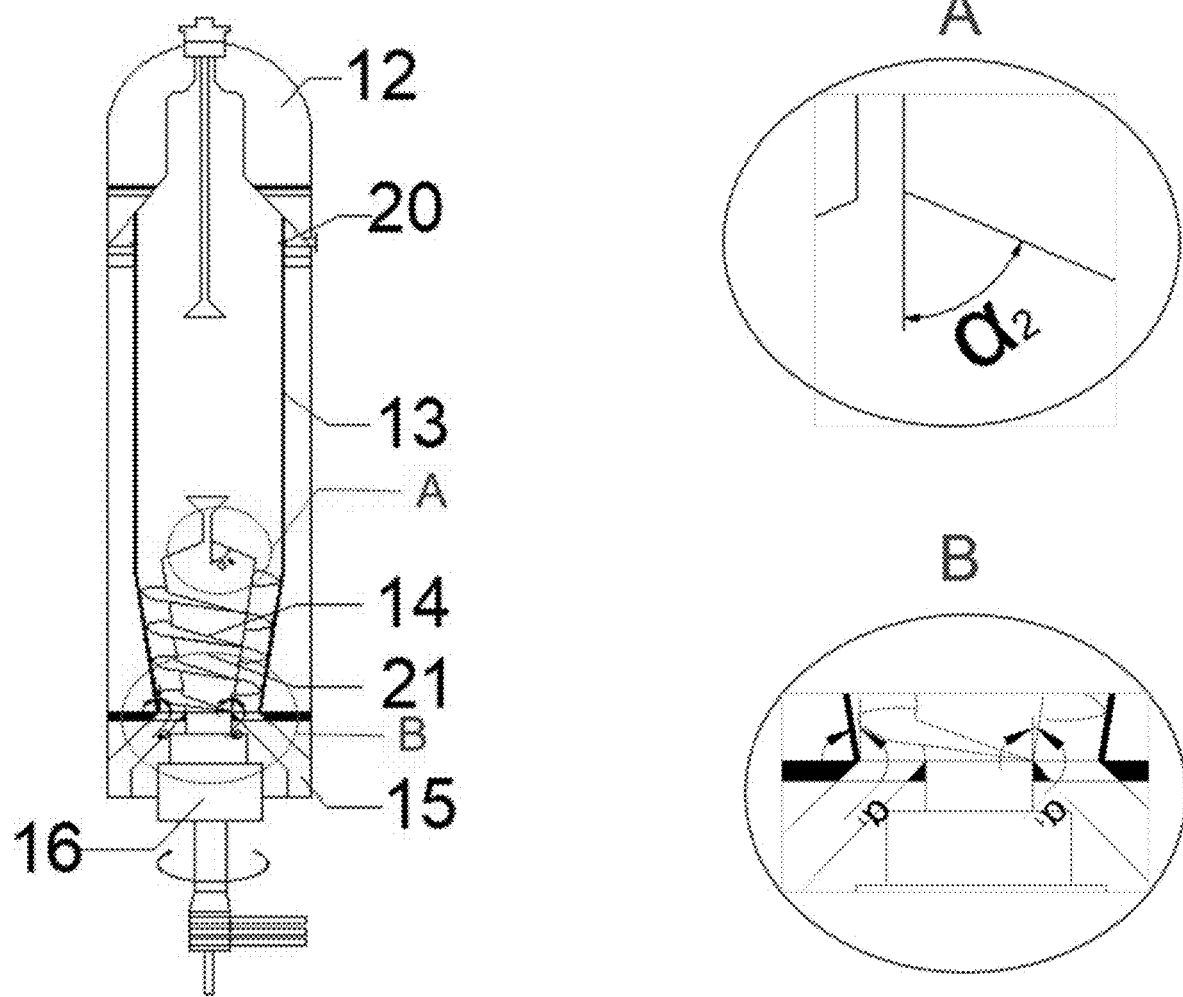
FIG. 2 shows a tube centrifuge (12) of the device for high pressure spray and counter-current precipitation extraction of herbal medicine.

Referring to FIG. 2, the tube centrifuge (12) includes the rotating tube (13) that is connected to the differential (16). The extraction waste discharge device includes the spiral scraper (14), the differential (16), the inner tube (21), and the extraction waste discharge outlet (15). The differential (16)

is connected to the spiral scraper (14) via a shaft. The rotating tube (13) has a column shape at one end (and a truncated cone shape at the other end, and a half cone angle of 10 to 12°. The overflow outlet (20) has a diameter of 60 to 100 mm and has a center line that is perpendicular to a rotary axis of the rotating tube (13). The inner tube (21) has a double truncated cone shape, a bottom half cone angle $\alpha 1$ that is the same as the half cone angle of the rotating tube (13), a top half cone angle $\alpha 2$ of 60-65°, and a length that is one third of the length of the rotating tube (13). The spiral scraper (14) is a single-headed spiral made of a wear-resistant steel and has a blade thickness of 6-8 mm and a blade height of 30-35 mm, and a distance between the spiral scraper (14) and the rotating tune (13) is 1.5 mm to 2 mm.

Example 1

The extraction of flavonoids from herb *Pogonatherum crinitum* includes the following steps:

Step one, spray extraction: 200 kg of herb *Pogonatherum crinitum* was pulverized to 100 to 120 mesh fine powder. The fine powder and water, in a ratio of 7 L water/1 kg fine powder, to an agitation tank (1). The mixture was stirred at 90 r/min for 1 hour, was pumped by a first plunger pump (2), and was sprayed into an extraction tank (3) at a spraying speed of 500 L/h. Three-fourths of the extraction tank (3) was filled with water, and the mixture was sprayed 2 cm below the surface of water. Water was pumped from a second plunger pump (7) from an extracting solvent tank (6) and sprayed countercurrently from the bottom of the extraction tank (3) at a speed of 1200 L/h to conduct extraction and form an extraction solution. The pressure of the second plunger pump (7) is 3.5 MPa. The extraction is conducted at 25° C.

Step two, pressure filtration and concentration: the extraction solution from step one was discharged to a filter press (4) at a speed of 500 L/h and a pressure of 0.5 MPa via the outlet at the bottom of the extraction tank (3) to remove insoluble waste. The filtered extraction solution was stored in an extraction storage tank (5), and subsequently, pumped by a first centrifugal pump (8) to a vacuum concentration tank (10). The extraction solution was concentrated under −0.08 MPa and at 60° C. in the vacuum concentration tank (10) to form a concentrated extraction solution with a solution density of 1.2. Water was recycled to the extracting solvent tank (6) by a second centrifugal pump (9).

Step three, spray and countercurrent precipitation: the concentrated extraction solution was pumped by a third plunger pump (11) to a tube centrifuge (12) at a speed of 300 L/h. The rotating tube (13) has a column shape (diameter: 600 mm; height: 700 mm) at one end a truncated cone shape (half cone angle: 10°; height: 600 mm) at the other end. The overflow outlet (20) has a diameter of 80 mm. The inner tube (21) has a double truncated cone shape, a bottom half cone angle $\alpha 1$ of 10°, a top half cone angle $\alpha 2$ of 65°. The spiral scraper (14) has a blade thickness of 6 mm and a blade height of 30 mm, and a distance between the spiral scraper (14) and the rotating tune (13) is 1.5 mm. The rotating speed of the rotating tube (13) is 3000 r/min. Three-fourths of the tube centrifuge (12) was filled with 60% ethanol aqueous solution. The concentrated extraction solution was sprayed 2 cm below the surface of 60% ethanol aqueous solution. 60% ethanol aqueous solution was pumped from a precipitation solvent storage tank (18) by the fourth plunger pump (19) and sprayed countercurrently from the bottom of the tube centrifuge (12) at a speed of 1200 L/h and a pressure of 3.0 MPa to form a precipitation solution. The tube centrifuge (12) was spun at 3000 r/min. The supernatant was discharged via an overflow outlet (20) to a resting tank (17) at a speed of 600-900 L/h. The supernatant was stored in the resting tank (17) for 24 hours. The extraction waste was discharged through an extraction waste discharge outlet (15) by a spiral scraper (14).

Step four, concentrating reduced pressure and drying: the supernatant from the resting tank (17) was concentrated under reduced pressure to a solution of density of 1.3. The solution was dried by vacuum spray to obtain flavonoids at a yield of 93%.

Example 2

The extraction of phenolic compounds and nonpolar diterpenoid compounds from herb *Salvia miltiorrhiza* includes the following steps:

Same steps as Example 1 except that the rotating tube (13) has a column shape (diameter: 600 mm; height: 600 mm) at one end a truncated cone shape (half cone angle: 12°; height: 550 mm) at the other end; the overflow outlet (20) has a diameter of 100 mm; the inner tube (21) has a double truncated cone shape, a bottom half cone angle $\alpha 1$ of 12°, a top half cone angle $\alpha 2$ of 60°; the spiral scraper (14) has a blade height of 35 mm; and 85% ethanol aqueous solution was used precipitation solvent.

The phenolic compounds and nonpolar diterpenoid compounds were extracted at a yield of 90.2%.

Example 3

The extraction of saponins from herb *Panax notoginseng* includes the following steps:

Same steps as Example 1 except that the rotating tube (13) has a column shape (diameter: 600 mm; height: 600 mm) at one end a truncated cone shape (half cone angle: 12°; height: 550 mm) at the other end; the inner tube (21) has a double truncated cone shape, a bottom half cone angle $\alpha 1$ of 12°, a top half cone angle $\alpha 2$ of 60°; the spiral scraper (14) has a blade thickness of 8 mm and a distance between the spiral scraper (14) and the rotating tune (13) is 2 mm; and 70% ethanol aqueous solution was used precipitation solvent.

The saponins were extracted at a yield of 89.4%.

Example 4

The extraction of glycyrrhinic acid from herb *Glycyrrhiza uralensis* includes the following steps:

Same steps as Example 1 except that 10% ethanol aqueous solution containing 0.5% ammonia was used as extracting solvent; and 98% sulfuric acid was used as precipitation solvent.

The glycyrrhinic acid was extracted at a yield of 91.3%.

Example 5

The extraction of ginkgo polysaccharide from herb *Ginkgo biloba* includes the following steps:

Same steps as Example 1 except that anhydrous ethanol was used as precipitation solvent.

The ginkgo polysaccharide was extracted at a yield of 92.7%.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method for extracting an herbal medicine comprising:

step one, spray extraction:

pulverizing herbs to 100 to 120 mesh fine powder, adding the fine powder and an extracting solvent, in a ratio of 6-7 L extracting solvent/1 kg fine powder, to an agitation tank (1), stirring a mixture of the fine powder and extracting solvent at 80-100 r/min for 1-1.5 hours, spraying the mixture to an extraction tank (3) at a spraying speed of 400 to 600 L/h, adding first additional extracting solvent to fill two-thirds to three-fourths of the extraction tank (3), the mixture being sprayed 2-3 cm below a surface of the extracting solvent in the extraction tank (3), spraying countercurrently second additional extracting solvent from a bottom of the extraction tank (3) at a speed of 1000-1600 L/h to form an extraction solution, the second additional extracting solvent being pumped from an extracting solvent tank (6) at a pump pressure of 3.0-5.0 MPa, the step one, spray extraction being conducted at room temperature;

step two, pressure filtration and concentration:

discharging the extraction solution from step one to a filter press (4) to remove insoluble waste at a speed of 400-600 L/h and a pressure of 0.4-0.7 MPa to store at an extraction storage tank (5), pumping the extraction solution from the extraction storage tank (5) to a vacuum concentration tank (10), concentrating the extraction solution in the vacuum concentration tank (10) under 0.08 MPa to 0.1 MPa and at 60-80° C. to form a concentrated extraction solution with a solution density of 1.0-1.3, the extracting solvent being recycled to the extracting solvent tank (6);

step three, spray and countercurrent precipitation:

spraying the concentrated extraction solution to a tube centrifuge (12) at a speed of 200-400 L/h, adding a precipitation solvent to fill two-thirds to three-fourths of the tube centrifuge (12), the concentrated extraction solution being sprayed 2-3 cm below a surface of the precipitation solvent in the tube centrifuge (12), spraying countercurrently additional precipitation solvent from a bottom of the tube centrifuge (12) at a speed of 1000-1400 L/h and a pressure of 2.0-4.0 MPa to form a precipitation solution, centrifuging the precipitation solution and discharging a supernatant through an overflow outlet (20) of the tube centrifuge (12) to a resting tank (17) at a speed of 600-900 L/h, the supernatant being stored in the resting tank (17) for 24 hours; and step four, concentrating reduced pressure and drying:

concentrating the supernatant from the resting tank (17) under reduced pressure, drying by vacuum spray and freeze-dry to obtain the herbal medicine.

2. The method of claim 1, wherein the extracting solvent is water or 10% ethanol aqueous solution containing 0.5% ammonia.

3. The method of claim 1, wherein the precipitation solvent is 60% ethanol aqueous solution, 85% ethanol aqueous solution, anhydrous ethanol, or 98% sulfuric acid.

* * * * *